United States Patent
Leek et al.

(10) Patent No.: US 9,599,739 B2
(45) Date of Patent: Mar. 21, 2017

(54) MATERIAL-DISCERNING SENSING BY MEASUREMENT OF DIFFERENT POINTS OF IMPEDANCE

(71) Applicant: Texas Instruments Incorporated, Dallas, TX (US)

(72) Inventors: Alan H. Leek, Frisco, TX (US); Damian M. Szmulewicz, Addison, TX (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 178 days.

(21) Appl. No.: 14/480,838

(22) Filed: Sep. 9, 2014

(65) Prior Publication Data
US 2016/0070017 A1    Mar. 10, 2016

(51) Int. Cl.
| | |
|---|---|
| *H01Q 1/24* | (2006.01) |
| *H04B 17/12* | (2015.01) |
| *H04B 5/00* | (2006.01) |
| *G01R 27/26* | (2006.01) |
| *G01N 27/00* | (2006.01) |
| *G01V 3/02* | (2006.01) |

(52) U.S. Cl.
CPC ............... *G01V 3/02* (2013.01); *G01N 27/00* (2013.01)

(58) Field of Classification Search
CPC . H01Q 1/24; H04B 17/12; H04B 5/00; G01N 27/00; G01V 3/02; G01R 27/26
USPC .................. 345/173–178; 324/630, 658, 637; 340/686.6; 343/702
See application file for complete search history.

(56) References Cited

U.S. PATENT DOCUMENTS

| | | | |
|---|---|---|---|
| 2007/0194878 A1* | 8/2007 | Touge ..................... | G01S 7/282 340/5.2 |
| 2009/0017785 A1* | 1/2009 | Qian ........................ | H04B 1/30 455/307 |
| 2011/0012793 A1* | 1/2011 | Amm ..................... | H01Q 1/243 324/658 |
| 2011/0250928 A1* | 10/2011 | Schlub .................. | H04B 17/00 455/550.1 |

* cited by examiner

*Primary Examiner* — Arleen M Vazquez
*Assistant Examiner* — Neel Shah
(74) *Attorney, Agent, or Firm* — John R. Pessetto; Charles A. Brill; Frank D. Cimino (57) ABSTRACT

A material-discerning proximity sensor is arranged to include an antenna that is arranged to radiate a radio-frequency signal. A capacitive sensor is arranged to detect a change in capacitance of the capacitive sensor and to receive the radio-frequency signal. An electrical quantity sensor is arranged to detect a change of the received radio-frequency signal and a change of a radio-frequency signal at an output of the at least one band pass filter.

18 Claims, 4 Drawing Sheets

MATERIAL-DISCERNING SENSING BY MEASUREMENT OF DIFFERENT POINTS OF IMPEDANCE

BACKGROUND

Contemporary proximity sensing techniques are used to determine whether (and at what distance) an object has entered into a range of a proximity sensor of an autonomous electronic system. For example, a capacitive electrode is able to discern the proximal presence of an object and in response activate a function of the autonomous electronic system. However, conventional sensors often have difficulty determining the nature of the proximal object and/or the material(s) that comprise the object.

SUMMARY

A material-discerning proximity sensor that includes an antenna that is arranged to radiate a radio-frequency signal. A capacitive sensor is arranged to detect a change in capacitance of the capacitive sensor and to receive the radio-frequency signal. An electrical quantity sensor is arranged to detect a change of the received radio-frequency signal and a change of a radio-frequency signal at an output of the at least one band pass filter.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description—and claims—to refer to particular system components. As one skilled in the art will appreciate, various names may be used to refer to a component. Accordingly, distinctions are not necessarily made herein between components that differ in name but not function. In the following discussion and in the claims, the terms "including" and "comprising" are used in an open-ended fashion, and thus are to be interpreted to mean "including, but not limited to . . . " Also, the terms "coupled to" or "couples with" (and the like) are intended to describe either an indirect or direct electrical (including electromagnetic) connection. Thus, if a first device couples to a second device, that connection can be made through a direct electrical (including electromagnetic) connection, or through an indirect electrical connection via other devices and connections.

Figure 1:
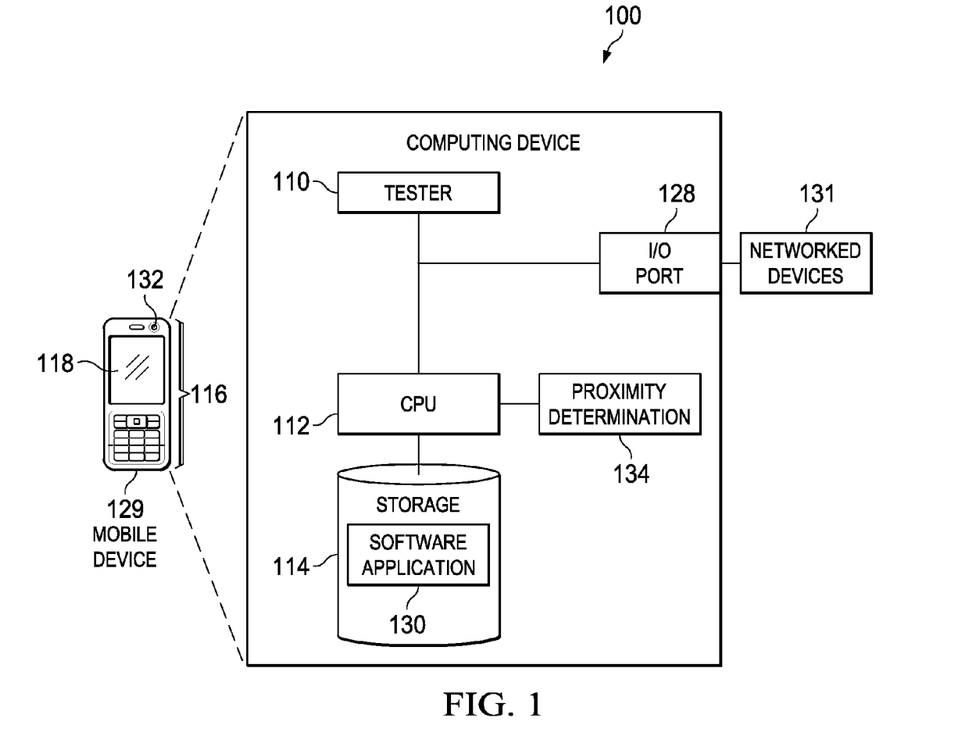
FIG. 1 shows an illustrative computing device in accordance with embodiments of the disclosure.

FIG. 1 shows an illustrative computing device 100 in accordance with embodiments of the disclosure. For example, the computing device 100 is, or is incorporated into, a mobile communication device 129, such as a mobile phone, a personal digital assistant (e.g., a BLACKBERRY® device), a personal computer, automotive electronics, projection (and/or media-playback) unit, or any other type of electronic system.

In some embodiments, the computing device 100 comprises a megacell or a system-on-chip (SoC) which includes control logic such as a CPU 112 (Central Processing Unit), a storage 114 (e.g., random access memory (RAM)) and tester 110. The CPU 112 can be, for example, a CISC-type (Complex Instruction Set Computer) CPU, RISC-type CPU (Reduced Instruction Set Computer), or a digital signal processor (DSP). The storage 114 (which can be memory such as on-processor cache, off-processor cache, RAM, flash memory, or disk storage) stores one or more software applications 130 (e.g., embedded applications) that, when executed by the CPU 112, perform any suitable function associated with the computing device 100. The CPU 112 can include (or be coupled to) a proximity determination 134 unit, which includes various components arranged in a common (or separate) substrate as disclosed herein below.

The tester 110 is a diagnostic system and comprises logic (embodied at least partially in hardware) that supports monitoring, testing, and debugging of the computing device 100 executing the software application 130. For example, the tester 110 can be used to emulate one or more defective or unavailable components of the computing device 100 to allow verification of how the component(s), were it actually present on the computing device 100, would perform in various situations (e.g., how the components would interact with the software application 130). In this way, the software application 130 can be debugged in an environment which resembles post-production operation.

The CPU 112 comprises memory and logic that store information frequently accessed from the storage 114. The computing device 100 is often controlled by a user using a UI (user interface) 116, which provides output to and receives input from the user during the execution the software application 130. The output is provided using the display 118, indicator lights, a speaker, vibrations, image projector 132, and the like. The input is received using audio and/or video inputs (using, for example, voice or image recognition), and mechanical devices such as keypads, switches, proximity detectors, and the like. The CPU 112 and tester 110 is coupled to I/O (Input-Output) port 128, which provides an interface (that is configured to receive input from (and/or provide output to) peripherals and/or computing devices 131, including tangible media (such as flash memory) and/or cabled or wireless media. These and other input and output devices are selectively coupled to the computing device 100 by external devices using wireless or cabled connections.

As disclosed herein, material-discerning proximity sensing techniques allow an autonomous electronic system to more accurately determine the substance of a proximal object by evaluating characteristics of materials that are included by the proximal object.

Figure 2:
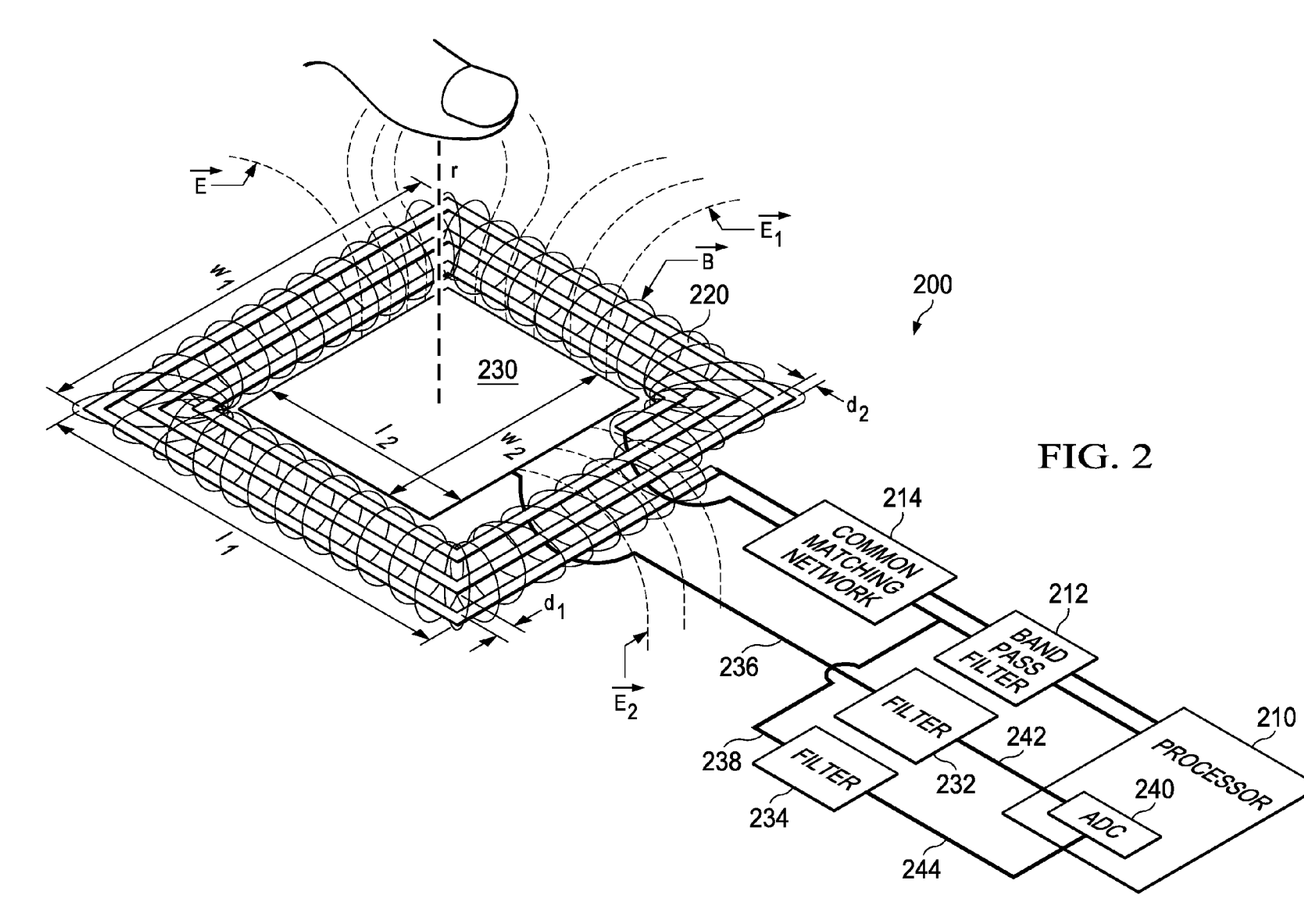
FIG. 2 is a schematic diagram illustrating a material-discerning sensing system in accordance with embodiments of the disclosure.

FIG. 2 is a schematic diagram illustrating a material-discerning proximity sensing system in accordance with embodiments of the present disclosure. System 200 is an example autonomous electronic system that is arranged to perform material-discerning sensing. System 200 includes a processor 210, a band pass filter 212, a, common matching network 214, an antenna 220, a capacitive proximity sensor 230, a first filter 232, a second filter 234 and an analog to digital (ADC) converter 240.

Processor 210 is a processor such as CPU 112 that is generally arranged to control functions of system 200 in response to the closeness of the material characteristics of proximal object, such as a human finger. Processor 210 generates and/or controls a single- or dual-ended radio-frequency signal that is adapted to drive antenna 220. The radio-frequency signal is a repetitive wave function, which can be a sine wave, a square wave, or other waveforms suitable for driving antenna 220. For example, a square wave signal can be filtered by band pass filter 212 to pass a fundamental frequency (at a frequency such as 13.56 megahertz). Common matching network 214 is arranged to balance the impedance of the feed lines to the antenna 220 with the characteristic impedance of the antenna 220.

In the illustrated embodiment, antenna 220 is arranged as a coil wherein the antenna, when energized, has an electrical core that extends through a portion of the surface of the capacitive proximity sensor 230. The coil of antenna 220 can be arranged as, for example, a series of conductive traces that progressively wind or loop (one or more times) around an inner portion of the capacitive sensor. When the conductive traces are arranged in a rectilinear fashion, each segment (or group of segments) is shorter (or longer, depending on a direction in which the segments are traversed) such that the segments progressively "spiral" inwards to (or outwards from, depending on the direction in which the segments are traversed) the capacitive proximity sensor 230. (In an alternate embodiment, the conductive traces can also be arranged using curved traces to form a curved spiral that is wound around the capacitive proximity sensor 230.)

The conductive traces have a length "$l_1$" that is longer than the length "$l_2$" of the capacitive proximity sensor 230 and a width "$w_1$" that is wider than the width "$w_2$" of the capacitive proximity sensor 230. Each segment of the conductive traces is separated (e.g., by a dielectric) from an adjacent segment of the conductive traces by a distance "$d_1$" and has a width of "$d_0$." Thus the conductive traces are arranged to be mutually inductive and form an electrical field in response to an applied (e.g., time invariant) radio-frequency signal (coupled from the processor 210, for example) being coupled to opposite end of the conductive traces. The conductive traces need not lie in the same plane as the capacitive proximity sensor 230, need not surround the capacitive sensor, and even have various shapes, but are arranged to electrically interact with the capacitive proximity sensor 230.

The total length of the conductive traces (as well as the number of "turns," the separation between adjacent segments, and width and length of each of the segments) can be selected in accordance with a fraction of the wavelength of the radio-frequency signal (e.g., tone and/or carrier wave) coupled to the antenna 220. The range "r" and directionality of the radiated electric field are also affected by the shape, proportions, trace width, distance between traces, total inner perimeter of the conductive traces and total outer perimeter of the conductive traces.

The electric field is illustrated using field lines $\vec{E}$, where field lines $\vec{E1}$ are generated in association with a capacitive sensor mode and field lines $\vec{E2}$ are generated in association with a radio frequency/material discernment mode. The field lines $\vec{E1}$ illustrate the electric field coupled between the object (to be detected) and the associated portions of the capacitive proximity sensor 230 and $\vec{E2}$ illustrate the electric field coupled between coil of antenna 220 and the associated portions of the capacitive proximity sensor 230. An upper and lower main lobe of the electric and magnetic fields can be used to detect the object (to be detected) having range "r." The electric field is also associated with magnetic components $\vec{F}$. Both conductive and non-conductive objects can possibly impact the strength of the $\vec{F}$ field of the coil antenna, which is associated with field lines $\vec{E2}$. Thus, in the material discernment mode, as the $\vec{F}$ field is impacted, the $\vec{E2}$ field is thus also impacted, which causes a change in the amplitude on the associated portions of the capacitive proximity sensor 230 (due to the changes in the $\vec{E2}$ field), for example.

Thus, the antenna 220 is arranged as a coil that, when energized, generates an electrical field having upper lobes and lower lobes, with a main upper lobe and main lower lobe defining an axis that extends through a portion of the surface of the capacitive proximity sensor 230 (as discussed below with respect to FIG. 3). When viewed as an orthogonal projection using an axis of projection (as viewed from above, for example) that is not parallel to a portion of the surface of the capacitive proximity sensor 230, the traces appear to surround the capacitive proximity sensor 230.

For ease of commercialization, the antenna that is arranged to radiate a radio-frequency signal can be driven using a transmit output power below the FCC threshold requiring certification (e.g., for a frequency band that includes the frequency of the radio-frequency signal coupled to the antenna 220).

Capacitive proximity sensor 230 is, for example, a copper fill pad having an area determined as the (multiplication) product of the length "$l_2$" and the width "$w_2$" of the capacitive proximity sensor 230. (The aspect ratio of a, for example, rectangular capacitive proximity sensor 230 can vary and the area thereof, for example, can be larger or smaller than the area of a human finger.) The copper fill pad of capacitive proximity sensor 230 is formed on a fixed substrate such as a printed circuit board (PCB) or formed on a flexible substrate such as a flexible PCB. As discussed above, in an embodiment coil antenna is arranged around the perimeter of the capacitive proximity sensor 230.

The capacitive proximity sensor 230 is arranged to discern the proximal presence of an object by detecting a change in capacitance of the capacitive sensor. The capacitive proximity sensor 230 is also used as a sensor for the discernment of the material of the proximal object by sensing the disruption (and the degree of disruption) of the electric field produced by antenna 220. Thus the capacitive proximity sensor 230 is used to make two differing types of measurements. In an embodiment, the measurements are time-multiplexed where the types of measurements are alternated.

System 200 uses the capacitive proximity pad in conjunction with an electrical quantity sensor such as an ADC (analog-to-digital converter) to measure the level at the applied frequency of the electrical field coupled to the capacitive proximity sensor 230 from the surrounding coil antenna 220. A function of the electrical quantity sensor is to quantify (in units of time, resistance, capacitance, and the like) a detected electrical property that is associated with the capacitive proximity pad. As various objects move into the field of the antenna, they impact and interfere with the tuning and efficiency of the antenna 220 and the common matching network 214 (which can be matched to the antenna 220). Objects in the field that are conductive affect characteristics of the magnetic field (and the concomitant electric field) output by the antenna 220 to a substantially greater degree than non-conductive objects. One characteristic of the characteristics of the electric field that is changed is manifested as a change in amplitude of the radio-frequency signal used to generate the electric and magnetic fields coupled to the capacitive proximity pad.

The change in amplitude of radio-frequency signal 236 can be detected by using measurements performed by the ADC 240. The ADC 240 forwards the measurements as data to be used by software and/or firmware of the processor 210. The first filter 232 is optionally employed to filter the received radio-frequency signal 236 to prevent and/or reduce aliasing of the sampled radio-frequency signal by the ADC 240.

The change in amplitude of radio-frequency signal 238 can be detected by using measurements performed by the ADC 240. The ADC 240 forwards the measurements as data to be used by software and/or firmware of the processor 210. The second filter 234 is optionally employed to filter the radio-frequency signal from the band pass filter 212 to prevent and/or reduce aliasing of the sampled radio-frequency signal by the ADC 240.

In an embodiment, a low-speed ADC 240 is used to minimize power consumption, complexity, and layout area. With the low-speed ADC 240, under-sampling and aliasing are intentionally used in a manner that allows for signal energy at the ADC 240 input to be detected while providing increased immunity to noise.

Without external filtering (to maintain a low cost, for example), the amplitude of the received radio signal frequency 236 can still be measured by the ADC 240 regardless of degree of aliasing caused by under-sampling (even given a large disparity in sampling rate and Nyquist rates with regards to the frequency of the radio-frequency signal). The capacitive proximity sensor 230 that is under-sampled by the ADC 240 thus effectively operates using a broadband input.

Without external filtering, the amplitude of the received radio signal frequency 238 can be measured by the ADC 240 regardless of degree of aliasing caused by under-sampling (even given a large disparity in sampling rate and Nyquist rates with regards to the frequency of the radio-frequency signal).

The total energy determined by the under-sampled ADC 240 inputs 242 and 244 is determined by, for example, summing the magnitude of the samples over a selected time period (e.g., a tenth of a second). (In an alternate embodiment, a software envelope detector can be arranged to determine the total energy.)

The amplitude of the sampled signal (even without the intervening presence of filter 232) is not substantially incorrectly measured by the ADC 240 when under-sampling the capacitive proximity sensor 230. The ADC 240 is able to substantially correctly measure the energy coupled to the capacitive proximity sensor 230 because the presence of a proximal conductive object (within range of the electric field) both lowers the energy (signal amplitude as determined by accumulating samples over a selected time period) at the input of the ADC 240, and also tends to shield the system 200 from external noise sources. Accordingly, under-sampling by the ADC 240 provides for increased noise immunity for the system, while also allowing the use of a relatively simple (e.g., low cost) broadband ADC 240 to measure the capacitive proximity sensor 230.

In other embodiments, more complex ADCs, comparators, sample and hold circuits, or other common peripherals or other various types of voltage sensors may be used to detect a change in amplitude of radio-frequency signals 236 and 238 coupled to capacitive proximity sensor 230. The detected change in amplitude of radio-frequency signals 236 and 238 coupled to capacitive proximity sensor 230 can be detected by accumulating samples over a selected time period using an electrical quantity sensor.

Figure 3:
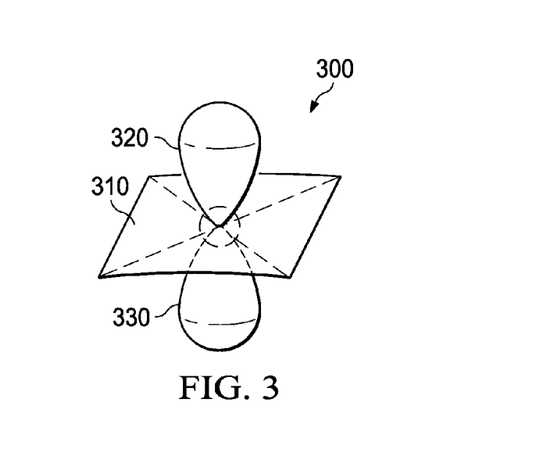
FIG. 3 is a schematic diagram illustrating radiated lobes of a material-discerning sensing sensor in accordance with embodiments of the disclosure.

FIG. 3 is a schematic diagram illustrating radiated lobes of a material-discerning proximity sensing sensor in accordance with embodiments of the disclosure. As shown in FIG. 2, antenna 220 is arranged as a coil that, when energized, generates an electrical field in response to a radio-frequency signal being coupled the antenna 220. In FIG. 3, the electric field 300 is illustrated as a main "lobe" of the generated having an upper lobe 320 and a lower lobe 330, the upper lobe 320 and lower lobe 330 defining an axis that extends through a portion of the surface of the (flexible) capacitive sensor 310. The upper lobe 320 and the lower lobe 330 are illustrated as geometric shapes for the sake of simplicity. In various embodiments the shape of the electric field varies in accordance with the various shapes and arrangements of the antenna 220 and the capacitive sensor 310.

Figure 4:
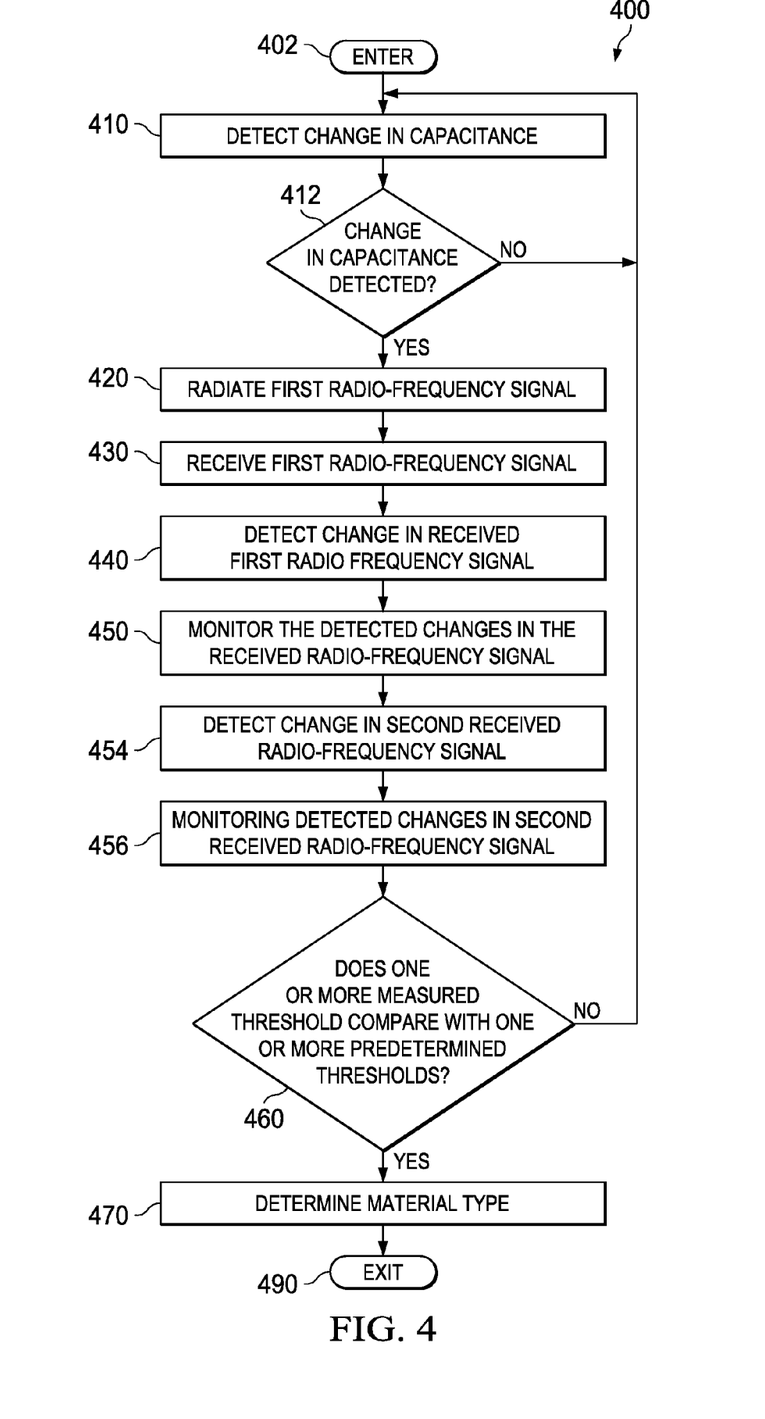
FIG. 4 is a flow diagram illustrating material-discerning sensing in accordance with embodiments of the disclosure.

FIG. 4 is a flow diagram illustrating material-discerning sensing in accordance with embodiments of the disclosure. The program flow illustrated herein is exemplary, and thus various operations within the program flow can be performed in an order that is not necessarily the same as the program flow illustrated herein. Program flow begins at node 402 and proceeds to operation 410.

In operation 410, a change in the capacitance of the capacitive sensor is detected. The capacitive change is detected using any suitable method including, for example, measuring an RC time-constant that is associated with the capacitive sensor. As discussed above, the change in capacitance can detect the proximity of an object, but substantially fails to discern the material that comprises the object. Program flow proceeds to operation 412.

In operation 412, a determination is made whether a change in capacitance has been detected. If a change in capacitance has not occurred, program flow proceeds to operation 410. If a change in capacitance has occurred, program flow proceeds to operation 420.

In operation 420, a radio-frequency signal 236 is radiated by an antenna that is substantially arranged around a capacitive sensor. The antenna is substantially arranged around the capacitive sensor when the radio-frequency signal 236 induces a voltage in the capacitive sensor. Program flow proceeds to operation 430.

In operation 430, the capacitive sensor receives the radio-frequency signal 236. A baseline measurement (such as when there is no object in the proximity of the capacitive sensor) of the magnitude of the radio-frequency signal 236 can be stored as a baseline measurement. The baseline measurement can be made by under-sampling (e.g., below Nyquist rates) the radio-frequency 236 signal using an ADC as described above to detect an energy level of the first radio-frequency signal received over a selected time period. The under-sampling also increases the relative amount of noise immunity of the system used to perform the material-discerning proximity sensing. The noise is typically generated externally to the system, although noise generated by the system is also possible. Program flow proceeds to operation 440.

In operation 440, a change in the radio-frequency signal 236 is detected. The change in the radio-frequency signal 236 is detected by measuring the magnitude of the first radio-frequency signal (using the under-sampling ADC, for example). Program flow proceeds to operation 450.

In operation 450, the detected changes in the radio-frequency signal 236 are monitored. The detected changes in the radio-frequency signal 236 are monitored by comparing the measured magnitude with the baseline measurement to determine the degree of the detected change. The change in the radio-frequency signal 236 can also be detected by measuring the magnitude of the radio-frequency signal 236 and comparing the measured magnitude with a predetermined threshold to determine the degree of detected change. The change in the radio-frequency signal 236 can also be detected by measuring the magnitude of the radio-frequency signal 236 and comparing the measured magnitude with a list of one or more thresholds that compare with predetermined thresholds that each correspond to a type of material of an object. Program flow proceeds to operation 454.

In operation 454, a change in the radio-frequency signal 238 from the output of the band pass filter 212 is detected. The change in the radio-frequency signal 238 is detected by measuring the magnitude of the radio-frequency signal 238 (using the under-sampling ADC, for example). Program flow proceeds to operation 456.

In operation 456, the detected changes in the radio-frequency signal 238 are monitored. The detected changes in the radio-frequency signal 238 are monitored by comparing the measured magnitude with the baseline measurement to determine the degree of the detected change. The change in the radio-frequency signal 238 can also be detected by measuring the magnitude of the radio-frequency signal 238 and comparing the measured magnitude with a predetermined threshold to determine the degree of detected change. The change in the radio-frequency signal 238 can also be detected by measuring the magnitude of the radio-frequency signal 238 and comparing the measured magnitude with a list of one or more thresholds that compare with predetermined thresholds that each correspond to a type of material of an object (such as a human finger) that would be used to make a valid proximity detection. Program flow proceeds to operation 460.

In operation 460, a determination is made whether one or more measured thresholds compare with one or more predetermined thresholds. Comparison of the measured thresholds of the received radio-frequency signals 236 and 238 with the predetermined thresholds provides an indication of the material that comprises a proximal object (e.g., that causes the detected change in capacitance). The measured magnitude is in direct proportion to the conductivity of the proximal object. If the measured thresholds compare with one or more predetermined thresholds, the program flow proceeds to operation 470. If the measure threshold do not compare with one or more predetermined thresholds, the program flow proceeds to operation 410.

In operation 470, the type of material is determined and estimated range of the object from the sensor. Program flow proceeds to node 490 and terminates.

Figure 5:
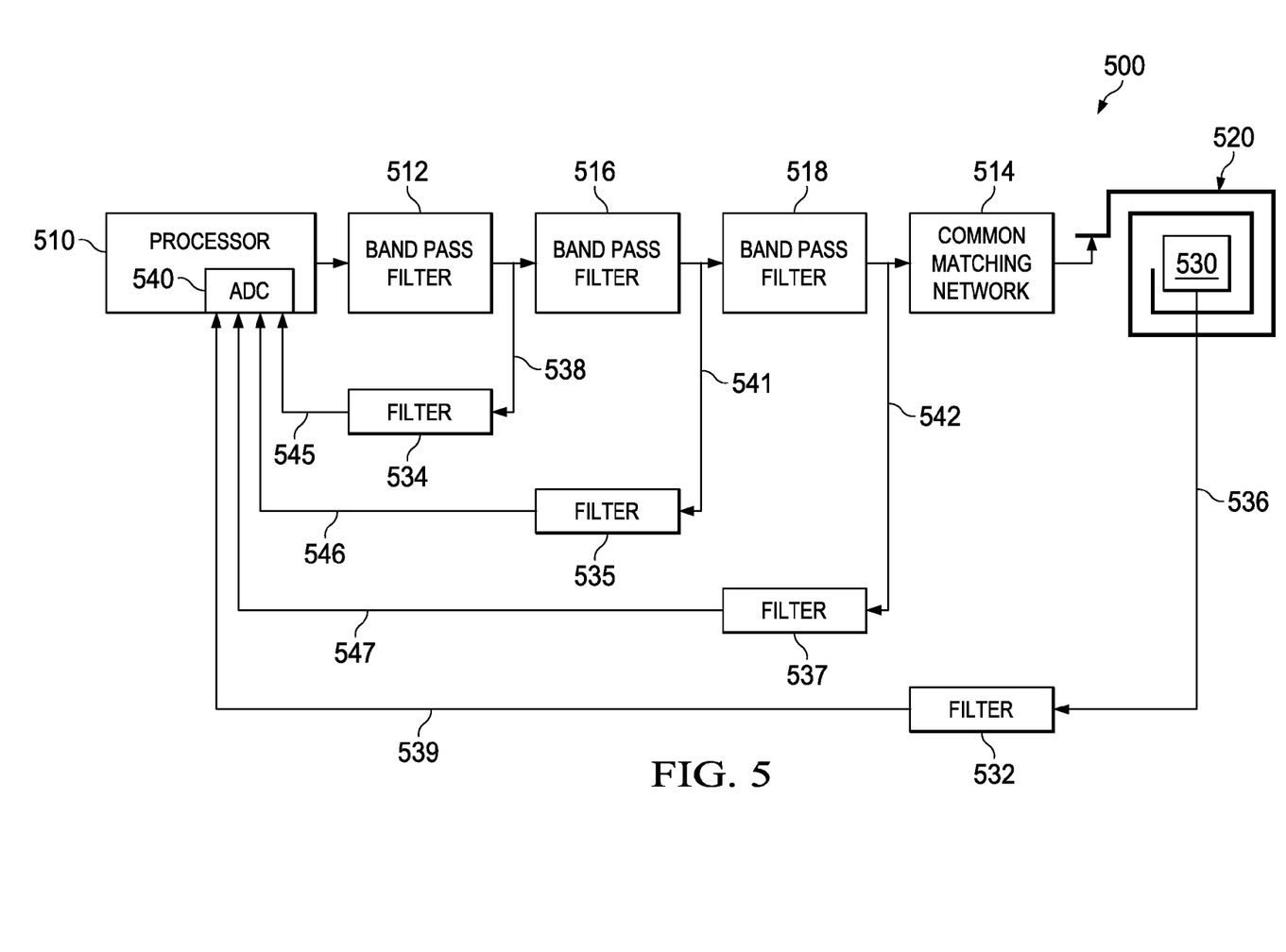
FIG. 5 is a schematic diagram illustrating a material-discerning sensing system in accordance with embodiments of the disclosure.

FIG. 5 is a schematic diagram illustrating a material-discerning sensing system in accordance with embodiments of the present disclosure. System 500 is an example autonomous electronic system that is arranged to perform material-discerning proximity sensing. System 500 includes a processor 510, three band pass filters 512, 516, 518, a common matching network 514, an antenna 520, a capacitive proximity sensor 530, a first filter 532, a second filter 534, a third filter 535, a fourth filter 537 and an analog to digital (ADC) converter 540.

Processor 510 is a processor such as CPU 112 that is generally arranged to control functions of system 500 in response to the closeness of the material characteristics of proximal object, such as a human finger. Processor 510 generates and/or controls a single- or dual-ended radio-frequency signal that is adapted to drive antenna 520. The radio-frequency signal is a repetitive wave function, which can be a sine wave, a square wave, or other waveforms suitable for driving antenna 520. For example, a square wave signal can be filtered by band pass filter 512 to pass a fundamental frequency (at a frequency such as 13.56 megahertz). Common matching network 514 is arranged to balance the impedance of the feed lines to the antenna 520 with the characteristic impedance of the antenna 520.

In the illustrated embodiment, antenna 520 is arranged as a coil wherein the antenna, when energized, has an electrical core that extends through a portion of the surface of the capacitive proximity sensor 530. The coil of antenna 520 can be arranged as, for example, a series of conductive traces that progressively wind or loop (one or more times) around an inner portion of the capacitive sensor. When the conductive traces are arranged in a rectilinear fashion, each segment (or group of segments) is shorter (or longer, depending on a direction in which the segments are traversed) such that the segments progressively "spiral" inwards to (or outwards from, depending on the direction in which the segments are traversed) the capacitive proximity sensor 530. (In an alternate embodiment, the conductive traces can also be arranged using curved traces to form a curved spiral that is wound around the capacitive proximity sensor 530.)

Thus, the antenna 520 is arranged as a coil that, when energized, generates an electrical field having upper lobes and lower lobes, with a main upper lobe and main lower lobe defining an axis that extends through a portion of the surface of the capacitive proximity sensor 530 (as discussed below with respect to FIG. 3). When viewed as an orthogonal projection using an axis of projection (as viewed from above, for example) that is not parallel to a portion of the surface of the capacitive proximity sensor 530, the traces appear to surround the capacitive proximity sensor 530.

For ease of commercialization, the antenna that is arranged to radiate a radio-frequency signal can be driven using a transmit output power below the FCC threshold requiring certification (e.g., for a frequency band that includes the frequency of the radio-frequency signal coupled to the antenna 520).

The capacitive proximity sensor 530 is arranged to discern the proximal presence of an object by detecting a change in capacitance of the capacitive sensor. The capacitive proximity sensor 530 is also used as a sensor for the discernment of the material of the proximal object by sensing the disruption (and the degree of disruption) of the electric field produced by antenna 520. Thus the capacitive proximity sensor 530 is used to make two differing types of measurements. In an embodiment, the measurements are time-multiplexed where the types of measurements are alternated.

System 500 uses the capacitive proximity pad in conjunction with an electrical quantity sensor such as an ADC (analog-to-digital converter) to measure the level at the applied frequency of the electrical field coupled to the capacitive proximity sensor 530 from the surrounding coil antenna 520. A function of the electrical quantity sensor is to quantify (in units of time, resistance, capacitance, and the like) a detected electrical property that is associated with the capacitive proximity pad. As various objects move into the field of the antenna, they impact and interfere with the tuning and efficiency of the antenna 520 and the common matching network 514 (which can be matched to the antenna 520). Objects in the field that are conductive affect characteristics of the magnetic field (and the concomitant electric field) output by the antenna 520 to a substantially greater degree than non-conductive objects. One characteristic of the characteristics of the electric field that is changed is manifested as a change in amplitude of the radio-frequency signal used to generate the electric and magnetic fields coupled to the capacitive proximity pad.

The change in amplitude of radio-frequency signal 536 can be detected by using measurements performed by the ADC 540. The ADC 540 forwards the measurements as data to be used by software and/or firmware of the processor 510. The first filter 532 is optionally employed to filter the received radio-frequency signal 536 to prevent and/or reduce aliasing of the sampled radio-frequency signal by the ADC 540.

The change in amplitude of radio-frequency signal 538 can be detected by using measurements performed by the ADC 540. The ADC 540 forwards the measurements as data to be used by software and/or firmware of the processor 510. The second filter 534 is optionally employed to filter the radio-frequency signal from the band pass filter 512 to prevent and/or reduce aliasing of the sampled radio-frequency signal by the ADC 540.

The change in amplitude of radio-frequency signal 541 can be detected by using measurements performed by the ADC 540. The ADC 540 forwards the measurements as data to be used by software and/or firmware of the processor 510. The third filter 535 is optionally employed to filter the radio-frequency signal from the band pass filter 516 to prevent and/or reduce aliasing of the sampled radio-frequency signal by the ADC 540.

The change in amplitude of radio-frequency signal 542 can be detected by using measurements performed by the ADC 540. The ADC 540 forwards the measurements as data to be used by software and/or firmware of the processor 510. The fourth filter 537 is optionally employed to filter the radio-frequency signal from the band pass filter 518 to prevent and/or reduce aliasing of the sampled radio-frequency signal by the ADC 540.

In an embodiment, a low-speed ADC 540 is used to minimize power consumption, complexity, and layout area. With the low-speed ADC 540, under-sampling and aliasing are intentionally used in a manner that allows for signal energy at the ADC 540 input to be detected while providing increased immunity to noise.

Without external filtering (to maintain a low cost, for example), the amplitude of the received radio signal frequency 536 can still be measured by the ADC 540 regardless of degree of aliasing caused by under-sampling (even given a large disparity in sampling rate and Nyquist rates with regards to the frequency of the radio-frequency signal). The capacitive proximity sensor 530 that is under-sampled by the ADC 540 thus effectively operates using a broadband input.

Without external filtering, the amplitude of the received radio signal frequencies 538, 541 and 542 can be measured by the ADC 540 regardless of degree of aliasing caused by under-sampling (even given a large disparity in sampling rate and Nyquist rates with regards to the frequency of the radio-frequency signal).

The total energy determined by the under-sampled ADC 240 inputs 539, 545, 546 and 547 is determined by, for example, summing the magnitude of the samples of the capacitive proximity sensor 530 (as affected by the electric field) over a selected time period (e.g., a tenth of a second) in which to accumulate samples. (In an alternate embodiment, a software envelope detector can be arranged to determine the total energy.) Thus; an unperturbed electric field, the presence of a non-conductive object within the electric field, and the presence of noise content do not substantially affect the baseline level of energy at the ADC 540 input.

The amplitude of the sampled signal (even without the intervening presence of filters 532, 534, 535 and 537 is not substantially incorrectly measured by the ADC 540 when under-sampling the capacitive proximity sensor 530. The ADC 540 is able to substantially correctly measure the energy coupled to the capacitive proximity sensor 530 because the presence of a proximal conductive object (within range of the electric field) both lowers the energy (signal amplitude as determined by accumulating samples over a selected time period) at the input of the ADC 540, and also tends to shield the system 500 from external noise sources. Accordingly, under-sampling by the ADC 540 provides for increased noise immunity for the system, while also allowing the use of a relatively simple (e.g., low cost) broadband ADC 540 to measure the capacitive proximity sensor 530.

In other embodiments, more complex ADCs, comparators, sample and hold circuits, or other common peripherals or other various types of voltage sensors may be used to detect a change in amplitude of radio-frequency signals 539, 545, 546 and 544.

The various embodiments described above are provided by way of illustration only and should not be construed to limit the claims attached hereto. Those skilled in the art will readily recognize various modifications and changes that could be made without following the example embodiments and applications illustrated and described herein, and without departing from the true spirit and scope of the following claims.

What is claimed is:

1. A material-discerning proximity sensing device comprising:
   an antenna that is arranged to radiate a radio-frequency signal;
   a capacitive sensor that is arranged to detect a change in capacitance of the capacitive sensor and that is arranged to receive the radio-frequency signal;
   an electrical quantity sensor that is arranged to detect a change of the received radio-frequency signal; and
   at least one band pass filter;
   wherein the electrical quantity sensor is arranged to detect a change in a radio-frequency signal at an output of the at least one band pass filter.

2. The device of claim 1 further comprising a matched network that is arranged to balance transmission characteristics of the antenna and the at least one band pass filter.

3. The device of claim 1 wherein the electrical quantity sensor comprises an analog to digital converter arranged to quantify the detected change of the received radio-frequency signal and the detected change of the radio-frequency at an output of the at least one band pass filter.

4. The device of claim 1 wherein the electrical quantity sensor comprises an analog to digital converter, the analog to digital converter arranged to quantify the detected change of the received radio-frequency signal and the detected change of the radio-frequency at an output of the at least one band pass filter using a sampling rate that is less-than-or-equal-to at least twice the frequency of a carrier wave of the transmitted radio-frequency signal.

5. The device of claim 4 wherein the analog to digital converter is arranged to quantify the detected change of the capacitance of the capacitive sensor.

6. The device of claim 5 wherein the analog to digital converter is arranged to output time-multiplexed readings of the received radio-frequency signal, the radio-frequency at an output of the at least one band pass filter and the capacitance of the capacitive sensor.

7. The device of claim 1 wherein the capacitive sensor is conductive material arranged having a surface.

8. The device of claim 7 wherein the surface of the capacitive sensor is planar.

9. The device of claim 7 wherein the antenna is arranged as a coil that when energized has an electrical core that extends through a portion of the surface of the capacitive sensor.

10. The device of claim 7 wherein the antenna is arranged as a series of conductive traces on a substrate that surround an inner portion of the capacitive sensor when viewed as a two-dimensional projection using an axis of projection that is not parallel to a portion of the surface of the capacitive sensor.

11. The device of claim 7 wherein the antenna is arranged as a coil that when energized, generates an electrical and magnetic field having an upper lobe and a lower lobe, the upper lobe and lower lobe defining an axis that extends through a portion of the surface of the capacitive sensor.

12. A material-discerning sensing system comprising:
an antenna that is arranged to radiate a radio-frequency signal;
a capacitive sensor that is arranged to detect a change in capacitance of the capacitive sensor and that is arranged to receive the radio-frequency signal;
a electrical quantity sensor that is arranged to detect a change of the received radio-frequency signal;
at least one band pass filter;
wherein the electrical quantity sensor is arranged to detect a change in a radio-frequency signal at an output of the at least one band pass filter; and
a processor that is arranged to monitor detected changes of the received radio-frequency signal and detected changes in the radio-frequency signal at an output of the at least one band pass filter and in response to the detected changes of the received radio-frequency signal and detected changes in the radio-frequency signal at an output of the at least one band pass filter determine a type of material.

13. The system of claim 12 wherein the processor is arranged to monitor detected changes in capacitance of the capacitive sensor, monitor the detected changes of the received radio-frequency signal and monitor the changes in the radio-frequency signal at an output of the at least one band pass filter and in response determine a type of material.

14. The system of claim 12 wherein the determination of a type of material is made in response to a comparison of the detected changes with a predetermined threshold.

15. A method for material-discerning sensing comprising:
radiating a radio-frequency signal using an antenna;
detecting a change in capacitance of a capacitive sensor;
receiving the radio-frequency signal using the capacitive sensor;
detecting a change of the received radio-frequency signal;
detecting a change in a radio-frequency signal at an output of the at least one band pass filter;
monitoring the detected changes of the received radio-frequency signal;
monitoring the detected changes in a radio-frequency signal at an output of the at least one band pass filter; and
determining the type of material in response to the detected changes of the received radio-frequency signal and the detected changes in a radio-frequency signal at an output of the at least one band pass filter.

16. The method of claim 15 comprising:
monitoring detected changes in capacitance of the capacitive sensor; and
determining the material type in response to the detected changes in capacitance of the capacitive sensor, the detected changes in a radio-frequency signal at an output of the at least one band pass filter and the detected changes of the received radio-frequency signal.

17. The method of claim 16 wherein the determination type of material is made in response to a comparison of the detected changes with a predetermined threshold.

18. The method of claim 15 comprising using an analog to digital converter to quantify detected changes of the received radio-frequency signal and detected changes in a radio-frequency signal at an output of the at least one band pass filter using a sampling rate that is less-than-or-equal-to at least twice the frequency of a carrier wave of the transmitted radio-frequency signal.

\* \* \* \* \*